United States Patent [19]

Akui et al.

[11] Patent Number: 5,577,991
[45] Date of Patent: Nov. 26, 1996

[54] THREE-DIMENSIONAL VISION ENDOSCOPE WITH POSITION ADJUSTMENT MEANS FOR IMAGING DEVICE AND VISUAL FIELD MASK

[75] Inventors: Nobuaki Akui, Hino; Satoshi Honma, Hachioji; Iwao Kanamori, Yokohama; Susumu Takahashi, Iruma; Toyoharu Hanzawa, Fuchu; Takashi Fukaya, Hachioji; Hitoshi Karasawa, Hachioji; Tetsumaru Kubota, Hachioji; Toshihiko Hashiguchi, Sagamihara; Akihiko Mochida, Hachioji; Akihiro Taguchi, Hachioji; Akio Nakada, Hachioji; Kenji Yoshino, Hachioji; Atsushi Kidawara, Tachikawa, all of Japan

[73] Assignee: Olympus Optical Co., Ltd., Tokyo, Japan

[21] Appl. No.: 499,648

[22] Filed: Jul. 7, 1995

Related U.S. Application Data

[63] Continuation of Ser. No. 73,321, Jun. 8, 1993, abandoned.

[30] Foreign Application Priority Data

Jun. 9, 1992 [JP] Japan .................... 4-149703
Nov. 18, 1992 [JP] Japan .................... 4-309074

[51] Int. Cl.⁶ .................................................. A61B 1/04
[52] U.S. Cl. .................... 600/111; 600/181; 600/109; 348/45
[58] Field of Search .................... 348/42, 45, 47, 348/49, 75; 600/103, 109, 111, 112, 166, 181; 359/377

[56] References Cited

U.S. PATENT DOCUMENTS

| | | | |
|---|---|---|---|
| 3,670,097 | 6/1972 | Jones | 348/49 |
| 3,959,580 | 5/1976 | Chocol et al. | 348/42 |
| 4,009,526 | 3/1977 | Abe et al. | 359/377 |
| 4,364,629 | 12/1982 | Lang et al. | 128/6 X |
| 4,395,731 | 7/1983 | Schoolman | 128/4 X |
| 4,702,571 | 10/1987 | Barber | 359/377 |
| 4,862,873 | 9/1989 | Yajima et al. | 128/6 |
| 4,924,853 | 5/1990 | Jones, Jr. et al. | |
| 5,063,441 | 11/1991 | Lipton et al. | 348/47 |
| 5,119,189 | 6/1992 | Iwamoto et al. | 348/47 |
| 5,222,477 | 6/1993 | Lia | 128/6 |
| 5,305,121 | 4/1994 | Moll | 348/45 |

*Primary Examiner*—Richard J. Apley
*Assistant Examiner*—John P. Leubecker
*Attorney, Agent, or Firm*—Armstrong, Westerman, Hattori, McLeland & Naughton

[57] ABSTRACT

A three-dimensional vision endoscopic apparatus according to the present invention comprises a pair of optical systems for transmitting an image of a subject as two subject images having a parallax between them, a pair of imaging devices for picking up subject images transmitted by the optical systems, at least one visual field mask, a display unit for displaying the two subject images alternately or concurrently, an adjusting mechanism for adjusting the position of one or both of the imaging devices so that the display images will become consistent on the screen of the display unit, and an adjusting mechanism for adjusting the relative position of the visual field mask.

2 Claims, 15 Drawing Sheets

FIG.4(a)
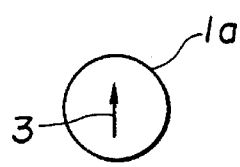
FIG.4(b)
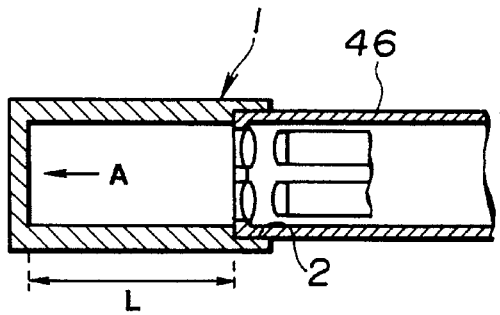
FIG.5
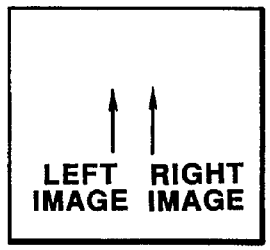
POSITION B
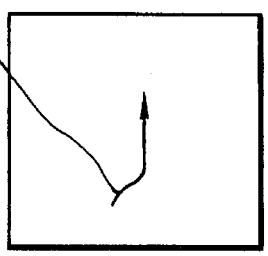
POSITION C
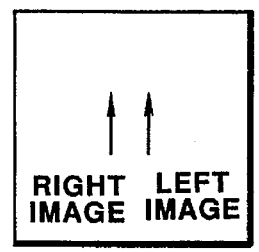
POSITION D
FIG.6
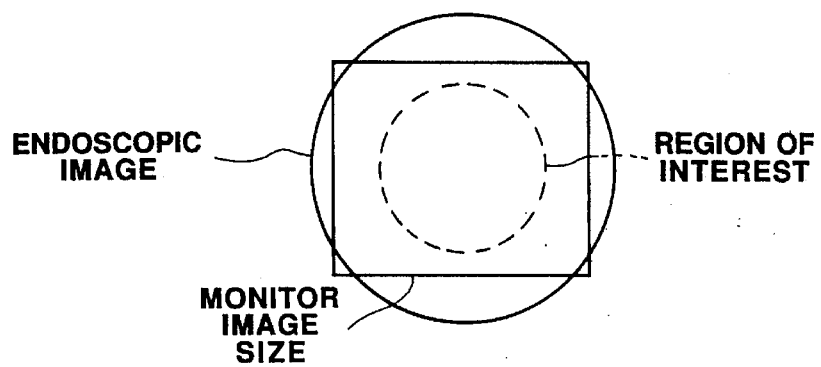

FIG.7  *PRIOR ART*
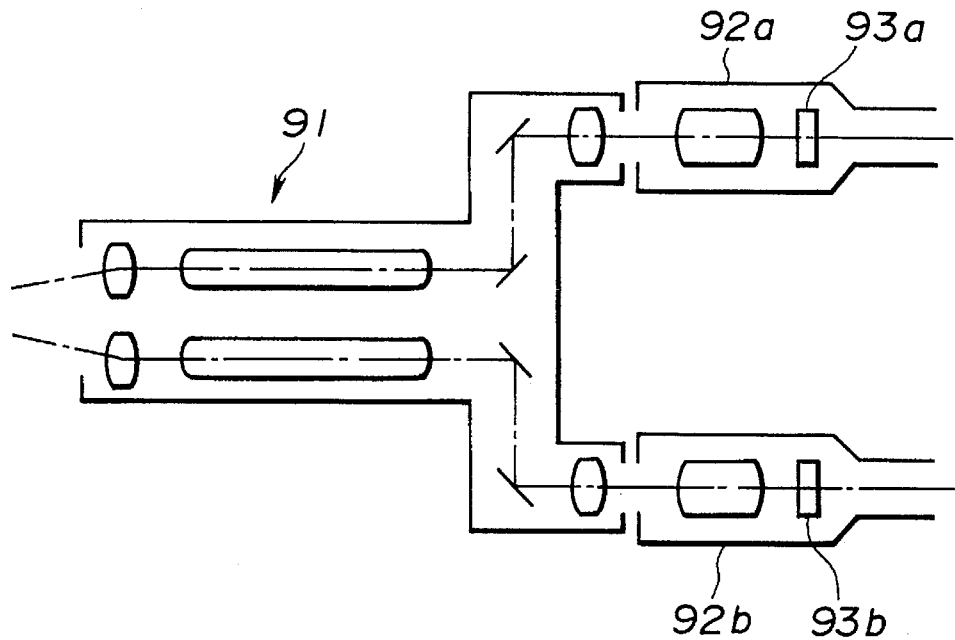
FIG.8
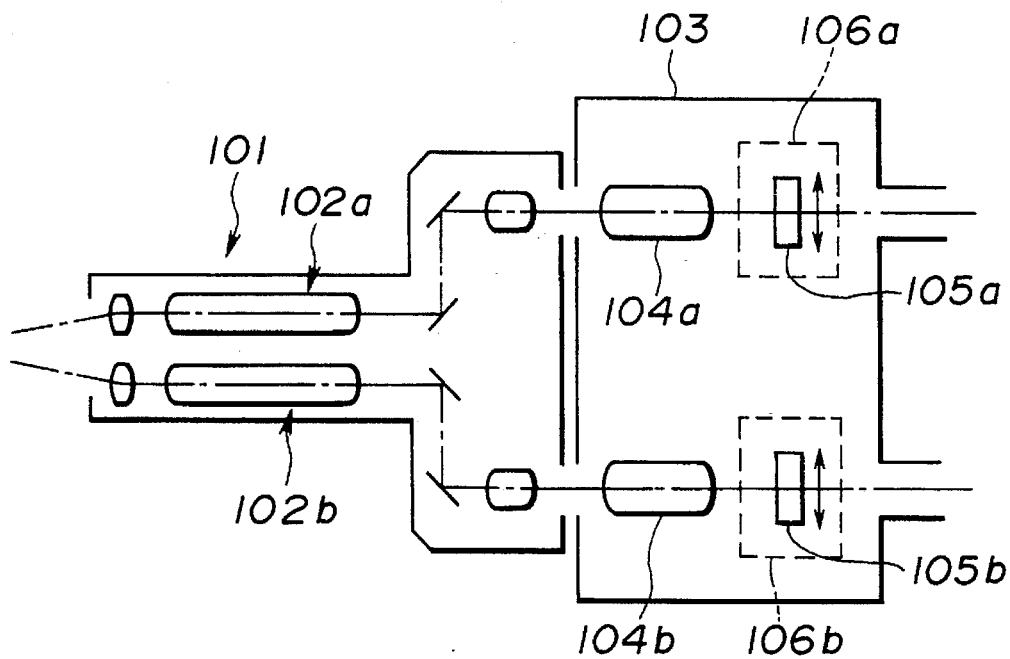

THREE-DIMENSIONAL VISION ENDOSCOPE WITH POSITION ADJUSTMENT MEANS FOR IMAGING DEVICE AND VISUAL FIELD MASK

This application is a continuation of application Ser. No. 08/073,321 filed Jun. 8, 1993, now abandoned.

BACKGROUND OF THE INVENTION

1. Field of the Invention

The present invention relates to a three-dimensional vision endoscope apparatus for three-dimensionally displaying a subject for observation.

2. Description of the Related Art

In recent years, endoscopes permitting observation of organs in body cavities and enabling a variety of treatment procedures have been put to use. Endoscopes for industrial use have been utilized to observe and inspect boilers, gas-turbine engines, pipes in a chemical plant, and insides of engines of automobiles in order to see if flaws and corrosion are present.

The endoscope for observing organs in body cavities falls into a class of a flexible endoscope whose insertional part is flexible and insertable into a body cavity through the oral cavity for observation and evaluation of a lesion, and a rigid endoscope whose insertional part is rigid and insertable straight into an intended region for observation and evaluation of a lesion.

The flexible endoscope, which is of an optical type, employs flexible image guide fibers as an image transmitting means. The rigid endoscope offers excellent sniping efficiency because of the rigid insertional part thereof, wherein a relay optical system is usually employed as an image transmitting means.

The endoscope including the rigid endoscope is divided into a type that permits observation of an optical image with naked eyes and a type that uses a solid-state imaging device such as a charge coupled device (CCD) as an imaging means. Whichever type of endoscope is employed, the inside of a body cavity that is an object of examination is visualized as, for example, a plane without depth perception. It is, therefore, difficult to observe the fine irregularities on the surface of an inner wall of a body cavity that provide a very important diagnostic guideline.

Japanese Patent Laid-Open No. 57-69839 has proposed, for example, a three-dimensional vision endoscope in which ends of a pair of image guides are provided with objective lenses and the other ends thereof are provided with eyepieces. In the three-dimensional vision endoscope, the pair of image guides are lying through an insertional part of the endoscope and a convergence angle formed between an objective lens and an object point of observation is set to an angle permitting three-dimensional vision. Thus, stereoscopic observation is enabled.

The foregoing three-dimensional vision endoscope is based on a flexible endoscope. In a three-dimensional vision endoscope based on a rigid endoscope (hereinafter, referred to as a three-dimensional vision rigid endoscope), two relay optical systems are placed in parallel with each other. Optical images provided by the two relay optical systems are processed by CCDs or the like, thus enabling three-dimensional observation. For example, U.S. Pat. No. 4,924,835 describes an arrangement that comprises two light transmitting means and two shutters, and that enables three-dimensional observation by shielding two observation images, which are provided by the light transmitting means, alternately using the shutters. The three-dimensional vision endoscope provides an observer with left and right optical images having a parallax between them. The observer looks into eyepieces through special glasses, and thus views a three-dimensional image. Alternatively, left and right images of a subject are displayed on a monitor to provide a three-dimensional image. The above three-dimensional vision endoscope is included in a three-dimensional vision rigid endoscope apparatus. The three-dimensional vision rigid endoscope apparatus converts an observation image into an electrical signal using an imaging means, processes the electrical signal, and then displays left and right images on a monitor screen concurrently or alternately.

In either of the techniques; that is, whether left and right images are displayed on a monitor concurrently or alternately, left and right images of a subject displayed on the monitor become consistent when viewed through the aforesaid glasses. Eventually, a stereoscopic image is observed.

However, in some three-dimensional vision rigid endoscopes each having two optical systems, the optical systems are formed independently of imaging means and made freely dismountable. In this kind of three-dimensional vision rigid endoscope, when optical systems, which are different from each other in orientation of a visual field, angle of view, and picture size, are used in combination with imaging means, the optical axes of the optical systems may become misaligned to mismatch left and right images in an observation screen on a monitor. A difference in the magnification or depth of field between the optical systems may lead to a mismatch in display position between left and right images, which disables the capabilities for three-dimensional recognition of a visualized subject. The mismatch in display position between left and right images sometimes occurs due to a mechanical impact not only in a three-dimensional vision rigid endoscope in which optical systems are dismountable but in a three-dimensional vision endoscope in which optical systems are united with imaging means.

The left and right images have a parallax between them. Even when the contours of the left and right images are mismatched, if a quantity of mismatch in display position between the left and right images is within an approximate range, an observer can see a consistent image while having no sense of unnaturalness but a sense of three-dimensionality.

However, when a quantity of mismatch in display position between left and right images is too large, the left and right images do not become consistent with each other. The observed image is therefore not recognized three-dimensionally, which causes an observer to feel terrible fatigue. Thus, the three-dimensional visualization procedure has been found a nuisance.

SUMMARY OF THE INVENTION

An object of the present invention is to provide a three-dimensional vision endoscope apparatus in which a quantity of mismatch in display position between two subject images on a display screen, which results from a mismatch between optical axes, can be calibrated to fall into a range providing optimal three-dimensionality thus causing an observer to feel less fatigued.

Briefly, a three-dimensional vision endoscope apparatus according to the present invention comprises a pair of optical systems for transmitting an image of a subject as two subject images having a parallax between them, a pair of imaging means for imaging the subject images transmitted by the optical systems, a display means for alternately or concurrently displaying two subject images having a parallax between them which have been picked up by the imaging means, and adjusting means for adjusting display images of objects located at specified distances from positions at which subject images enter the optical systems, so that the display images of the objects will become consistent with each other on a screen of the display means.

Other features and advantages of the present invention will be apparent from the description below.

BRIEF DESCRIPTION OF THE DRAWINGS

FIG. 4a shows a reference image formed on the bottom of a calibrator;

FIG. 4b is a cross-sectional view of the calibrator for a three-dimensional vision rigid endoscope;

FIG. 5 is an explanatory diagram showing a quantity of mismatch between images resulting from a difference in the position of a reference image;

FIG. 6 is an explanatory diagram for imaging ranges comparing contours of images;

FIG. 7 is an explanatory diagram showing a schematic arrangement of a general three-dimensional vision endoscope apparatus;

FIG. 8 is an explanatory diagram showing a schematic arrangement of a three-dimensional vision endoscope apparatus having adjusting means for mechanically adjusting the relative positions of optical systems with respect to CCDs;

DETAILED DESCRIPTION OF THE PREFERRED EMBODIMENTS

Referring to FIGS. 1 to 5, the first embodiment will be described.

A three-dimensional vision endoscope apparatus in this embodiment employs a rigid endoscope.

Figure 1:
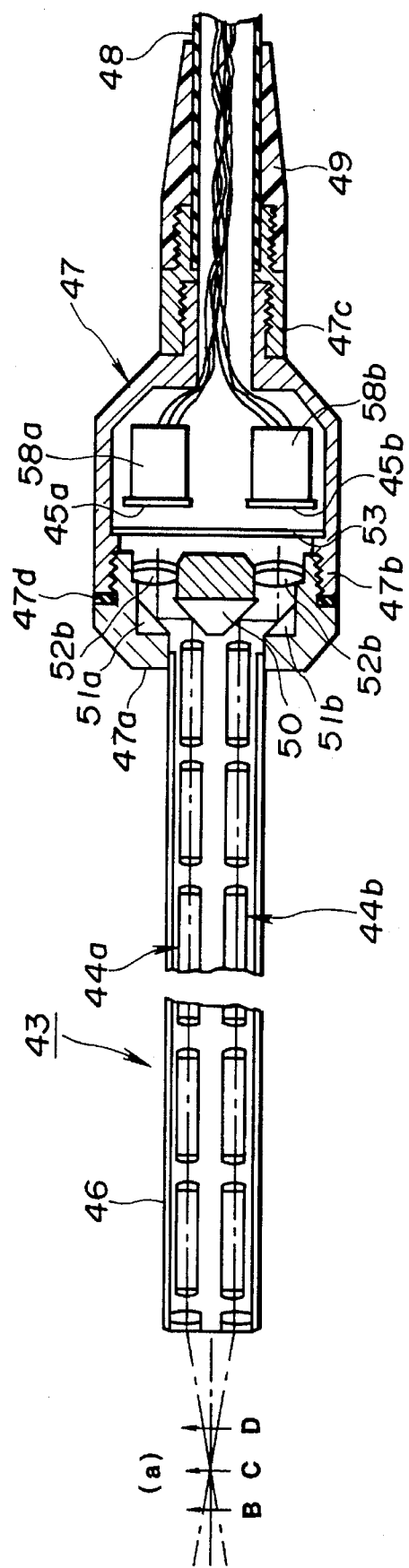
FIG. 1 is a cross-sectional view showing a structure of a three-dimensional vision rigid endoscope.

A three-dimensional vision endoscope 43 shown in FIG. 1 includes relay optical systems 44a and 44b designed for three-dimensional observation, and CCDs 45a and 45b for picking up subject images transmitted by the relay optical systems 44a and 44b. Thus, the three-dimensional vision endoscope 43 produces left and right subject images having a parallax between them.

Figure 2:
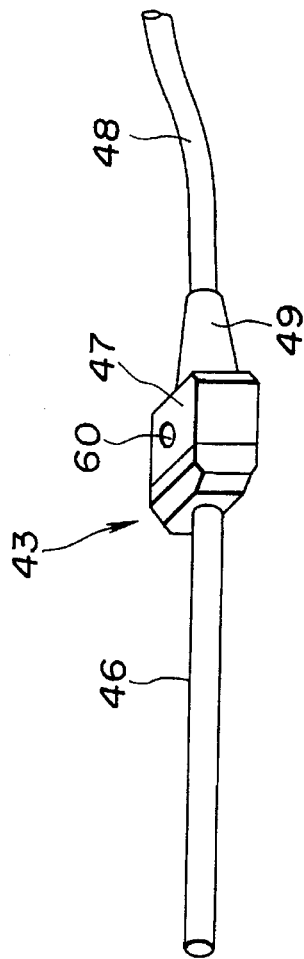
FIG. 2 is an oblique view of the three-dimensional vision rigid endoscope.

As shown in FIG. 2, the three-dimensional vision rigid endoscope 43 includes a rigid insertional part 46, and an operational part holder 47 coupled with the insertional part 46. A cable 48 extends from the back of the operational part holder 47. The relay optical systems 44a and 44b are incorporated in the insertional part 46.

As shown in FIG. 1, the operational part holder 47 consists of a cover member 47a serving as a distal portion and a holder body 47b engaged with the back end of the cover member 47a. The holder body 47b has a back member 47c which engages with a projection projecting behind the holder body. A member for shielding the cable 48, for example, a cable bend protector 49 made of a resin, is engaged with the back end of the back member 47c. A seal member 47d is interposed between the cover member 47a and holder body 47b, thus tightly shutting out water from an internal space to be created when the cover member 47a is engaged with the holder body 47b.

A prism 50, which reflects subject images transmitted by the relay optical systems 44a and 44b in directions perpendicular to the optical axes of the optical systems, is placed in the cover member 47a of the operational part holder 47. In addition, mirrors 51a and 51b for reflecting two subject images reflected from the prism 50 in directions parallel with the optical axes of the relay optical systems, and image formation lenses 52a and 52b for forming images reflected from the mirrors 51a and 51b are incorporated in the cover member 47a.

A cover glass 53 is placed in the vicinity of a distal opening of the holder body 47b of the operational part holder 47. The holder body 47b includes the CCDs 45a and 45b which receive and pick up two subject images formed by the image formation lenses 52a and 52b via the cover glass 53. Peripheral circuits 58a and 58b are connected to the back ends of these CCDs 45a and 45b.

Figure 3:
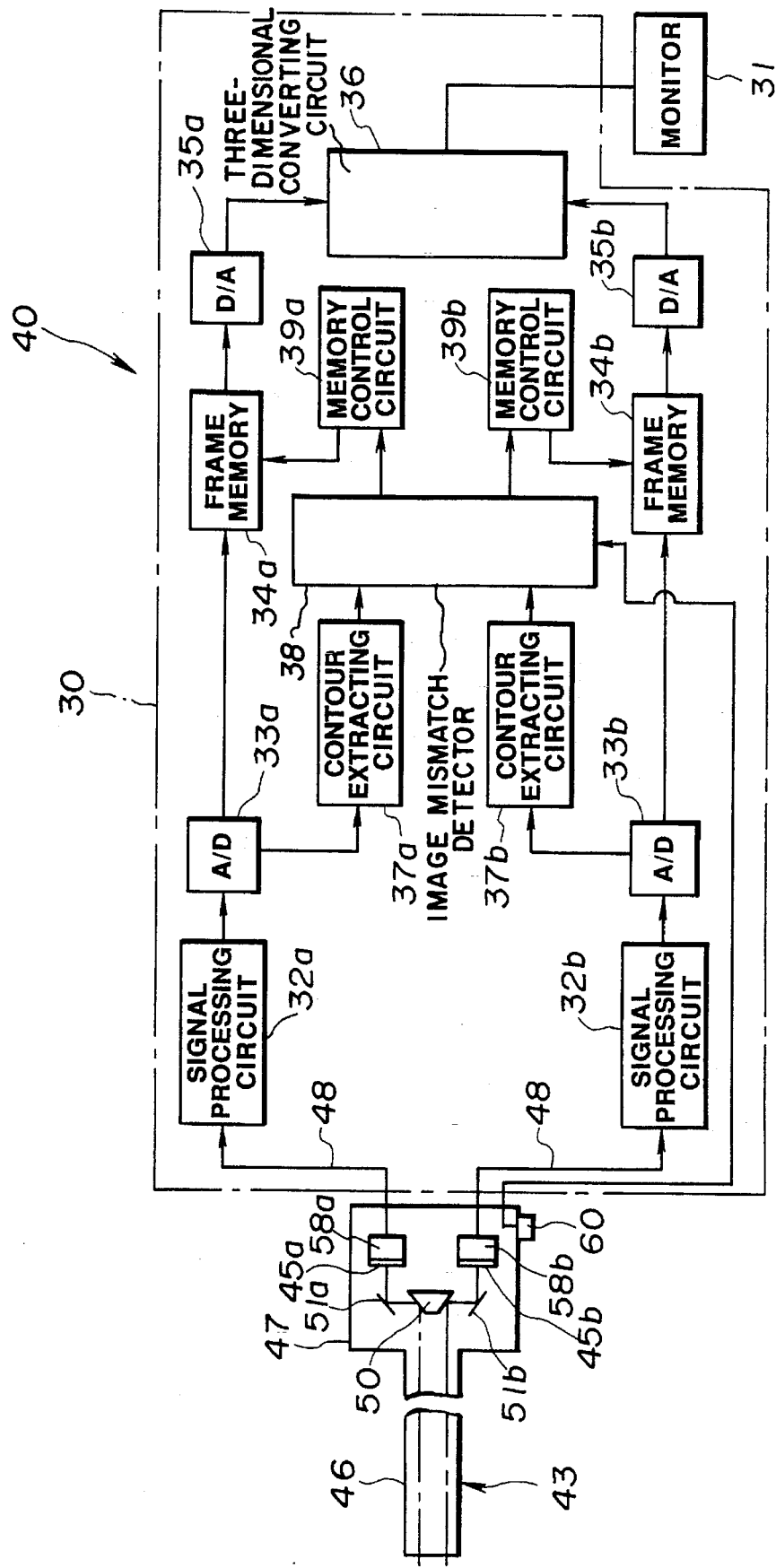
FIG. 3 shows a configuration of a three-dimensional vision rigid endoscope apparatus.

The CCDs 45a and 45b convert formed left and right subject images into electric signals respectively, and output the electric signals to a control unit 30 shown in FIG. 3 over a cable 48.

An illumination optical system, which is not shown, is incorporated in the three-dimensional vision rigid endoscope 43. Illumination light is supplied from the control unit 30 to the illumination optical system.

As shown in FIG. 3, the control unit 30 is electrically coupled with the three-dimensional vision rigid endoscope 43 over the cable 48. The control unit 30 drives the CCDs 45a and 45b, processes output electrical signals, and displays left and right subject images on a monitor 31 alternately at a rate of, for example, 30 times per second. When an observer sees the subject images displayed on the monitor using interceptive glasses, the observer recognizes a stereoscopic image.

More particularly, the left and right interceptive glasses are alternately intercepted from light in synchronization with the display of an image. An after-image effect is then utilized to allow an observer to experience three-dimensionality. Since the left and right subject images transmitted by the two relay optical systems have a parallax between them, the images are seen as a single three-dimensional image.

In the three-dimensional vision rigid endoscope 43 shown in FIG. 1, the operational part holder 47 can be divided into an imaging section (proximal portion) including CCDs and an optical section (distal portion) including a prism. The proximal and distal portions can be easily united easily.

In other words, the optical section and imaging section can be attached to or detached from each other freely. The optical section can therefore be united with CCDs, which results in the improved operability of the three-dimensional vision endoscope 43. Furthermore, a variety of combinations are realized among optical systems, which differ from one another in the orientation of a visual field, magnification, picture size, and depth of field, and imaging means which differ from one another in the number of images.

The optical axes of the relay optical systems incorporated in the insertional part of the endoscope are angled using a prism and mirrors which constitute an optical path altering means. The three-dimensional vision rigid endoscope 43 can therefore employ large CCDs providing high resolution.

It is desirable that the insertional endoscope part is made smaller in diameter for greater insertional smoothness. To cope with this need, the two relay optical systems must be arranged as close to each other as possible. In the three-dimensional vision rigid endoscope 43, an optical path altering means is incorporated in the operational part holder 47 that may be larger in diameter to some extent, and the optical paths are designed to match the optical axes of two CCDs.

In the three-dimensional vision rigid endoscope 43, the optical path altering means may be installed in the imaging means.

FIG. 4b shows a cross section of a calibrator for a three-dimensional vision rigid endoscope relating to the present invention. FIG. 4a is an arrow-A view of FIG. 4b.

A calibrator 1 shown in FIG. 4b provides a reference in calibrating a quantity of mismatch between left and right subject images so that optimal three-dimensionality can be given at a specified position. The calibrator 1 has a cylindrical shape and forms an opening 2 at one end. The distal end of the insertional part of the three-dimensional vision rigid endoscope 43 is fitted into the opening 2 so as to be detached freely. A reference image 3 serving as a reference in calibrating a quantity of mismatch is, as shown in FIG. 4a, formed on the internal bottom 1a of the cylinder of the calibrator 1. In the calibrator 1, a distance L of the reference image 3 on the internal bottom from the distal surface of a fitted endoscope is determined so as to nullify a quantity of mismatch between left and right subject images.

The distance L in FIG. 4a is, in general, set to a distance of a subject, which is most frequently visualized using a three-dimensional vision endoscope, from the distal surfaces of objective lens systems. The distance L is, for example, 50 mm or 30 mm.

FIG. 5 shows a mismatch in display position between subject images displayed on a monitor. As illustrated, when the position shown in FIG. 1 at which a subject is imaged changes to a position B, position C, and position D, images displayed on the monitor vary. To be more specific, when a subject is imaged at the position C, the left and right images become consistent with each other to produce an easy-to-see image allowing an observer to experience three-dimensionality but feel less fatigued. The position B is too far, but the position D is too close. As a result, the left and right images are separated from each other, causing an observer to feel very fatigued.

Referring to FIG. 3, a signal processing system for producing a three-dimensional image and a circuitry for calibrating it, which are installed in the control unit 30, and the operation of the signal processing system and circuitry will be described below.

The control unit 30 comprises signal processing circuits 32a and 32b for performing gamma correction and other processing on electric signals provided by the CCDs 45a and 45b, A/D converters 33a and 33b for converting video signals provided by the signal processing circuits 32a and 32b from the analog form into the digital form, frame memories 34a and 34b for storing digitized outputs frame by frame, and D/A converters 35a and 35b for converting signals read from the frame memories 34a and 34b from the digital form into the analog form, The control unit 30 includes a three-dimensional conversion circuit 36 for displaying the outputs of the D/A converters 35a and 35b alternately on the monitor 31. When seeing images on the monitor 31 using interceptive glasses, an observer can observe an image of a subject having three-dimensionality.

As for a technique for realizing three-dimensional vision, the concurrent display of left and right images on two respective monitors may also apply instead of the alternate display of left and right images on the monitor 31.

The control unit 30 further includes contour extracting circuits 37a and 37b for extracting contours from images provided by the A/D converters 33a and 33b, an image mismatch detector 38 that compares the outputs of the contour extracting circuits 37a and 37b to detect a quantity of mismatch between images, and memory control circuits 39a and 39b that control reading of the frame memories 34a and 34b according to the output of the image mismatch detector 38.

The image mismatch detector 38 detects a quantity of mismatch when a button 60 formed on the operational part holder 47 of an endoscope is turned on. The memory control circuits 39a and 39b control the sequence of reading addresses in the frame memories 34a and 34b so as to cancel out a quantity of mismatch.

The control unit 30 may detect a quantity of mismatch only once. Alternatively, the image mismatch detector 38 may also detect a quantity of mismatch to confirm that the quantity of mismatch is within an appropriate range. When it is found that the quantity of mismatch exceeds the appropriate range, processing is restarted in order to cancel out the quantity of mismatch. Video signals read from the frame memories 34a and 34b are then displayed at substantially consistent positions on the monitor 31, allowing an observer to observe a subject image with three-dimensionality.

By the way, processing is usually done in the center of an image. The portion of a subject (for example, an organ) visualized as the periphery of an image is located at a distance different from the portion thereof visualized as the center thereof. A quantity of mismatch in the periphery of an image therefore differs from or is larger than that in the center thereof. When part of an endoscopic image is sampled to detect a quantity of mismatch between left and right images, as shown in FIG. 6, a region of interest serving as a sampling range is set to be smaller than an image size but include the center of the endoscopic image. Left and right images should therefore be compared with each other within the region of interest to detect a quantity of mismatch between the left and right images.

When the button 60 is off, the memory control circuits 39a and 39b compose a screen along with the read of standard video signals. The memory control circuits 39a and 39b control writing of the frame memories 34a and 34b.

The distance L in the calibrator 1 is set substantially identical of distance to the position C. Though a simple jig, this calibrator provides the three-dimensional rigid endoscope apparatus 40 of this embodiment with a reference for calibrating a quantity of mismatch between left and right images and thus permitting three-dimensionality at an optimal position. Since the calibration button 60 is formed on the operational part holder 47, once the button 60 is pressed, the control unit 30 operates to calibrate the mismatch in display position between left and right images. The control unit 30 controls reading of the frame memories 34a and 34b according to the quantity of mismatch detected by the image mismatch detector 38, and calibrates the quantity of mismatch in display position between left and right images. Consequently, the left and right images whose display positions have become substantially (optimally) consistent with each other are displayed on the monitor 31. An observer will therefore not feel fatigued but can observe a subject image with optimal three-dimensionality.

As described previously, this embodiment can calibrate mismatch between left and right subject images resulting from mismatch between optical axes. The three-dimensional vision rigid endoscope in this embodiment can calibrate the mismatch in display position between left and right images occurring with different optical systems, that is, optical systems different from each other, for example, in orientation of a visual field, angle of view, and picture size are combined with imaging means. The mismatch in display position between left and right images resulting from the difference in magnification or depth of field between optical systems can also be calibrated.

This embodiment includes an adjusting means that uses electrical signals provided by CCDs to perform electrical adjustment. An alternative adjusting means adjusts the mismatch between optical axes by driving optical systems mechanically or electrically. The button 60 may be a foot switch.

The three-dimensional vision endoscope apparatus in this embodiment may be based not only on a rigid endoscope but also on a flexible endoscope in which flexible image guide fibers are used instead of relay optical systems as light transmitting means.

Examples of adjusting means for adjusting optical systems mechanically will be described below.

In a three-dimensional vision endoscope apparatus, as shown in FIG. 7, built-in CCDs 93a and 93b are usually locked in TV cameras 92a and 92b serving as imaging means connected to eyepiece units in a three-dimensional vision endoscope 91. The positions of the CCDs 93a and 93b are fixed with respect to optical systems in the three-dimensional vision endoscope 91. To produce a high-quality observation image with three-dimensionality, the positions of images in the centers of visual fields must be aligned with the CCDs. However, since the CCDs are stationary, the images in the centers of visual fields may not align with the same points due to a variation between optical systems or a positional variation between CCDs. The images are therefore not seen as a subject image with three-dimensionality.

Figure 9:
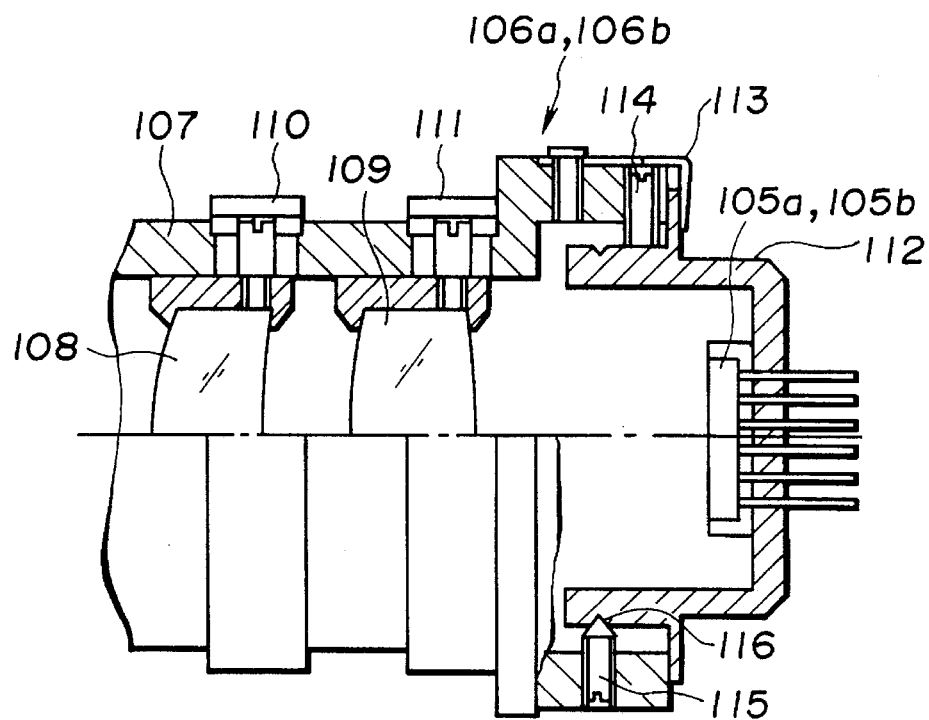
FIG. 9 is a partly cut-out cross-sectional view of a position adjusting mechanism for mechanically adjusting the relative position of an optical system with respect to a CCD.
Figure 10:
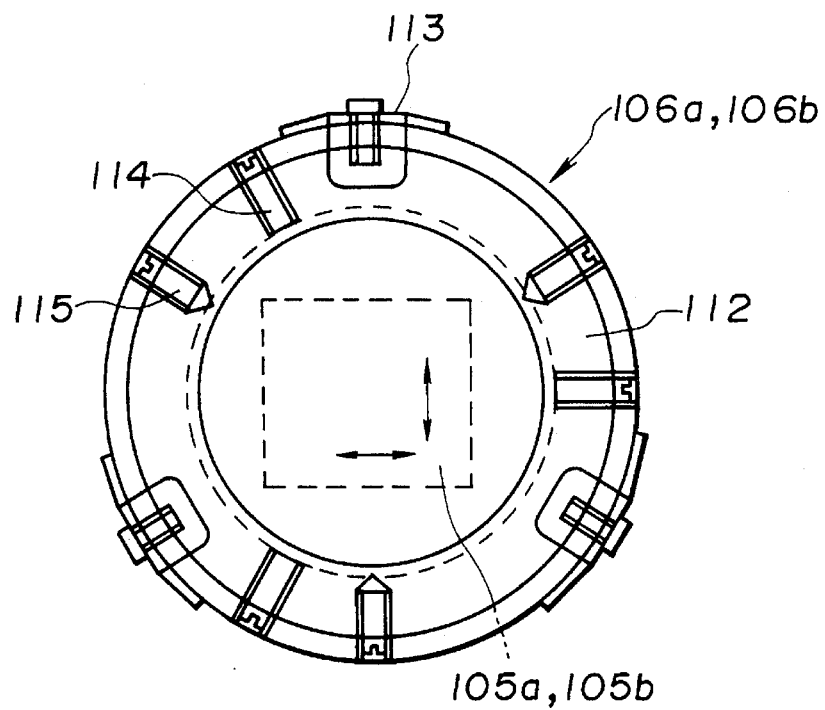
FIG. 10 is a plan view viewing the position adjusting mechanism in FIG. 9 from the back thereof.

As shown in FIGS. 8 to 10, adjusting means for adjusting the relative positions of CCDs with respect to optical systems are installed to permit three-dimensional vision.

As shown in FIG. 8, a three-dimensional vision endoscope 101 has two observation optical systems 102a and 102b. A TV camera 103 is coupled with the back ends of the observation optical systems 102a and 102b, and thus picking up two subject images having a parallax between them. The TV camera is an independent unit including image formation optical systems and CCDs which are incorporated in the operational part holder 47 in the previous embodiment.

The TV camera 103 includes image formation lenses 104a and 104b. CCDs 105a and 105b are arranged so as to pick up subject images at the image forming positions of the image formation lenses 104a and 104b. The CCDs 105a and 105b can be moved by position adjustment mechanisms 106a and 106b for adjusting the relative positions of the CCDs with respect to optical systems.

The structure of the position adjustment mechanism 106a or 106b will be described with reference to FIGS. 9 and 10. FIG. 10 views FIG. 9 from the back thereof (CCD).

A lens barrel 107 includes a focusing lens system 108 and a variable magnification lens system 109 which are held by adjustment frames 110 and 111, respectively. For focusing or other adjustment, the adjustment frames 110 and 111 are manipulated to achieve focusing or adjustment of a magnification.

A CCD frame 112 is attached to the back end of the lens barrel 107. In the CCD frame 112, a CCD 105a or 105b is locked. The CCD frame 112 can be displaced with respect to the lens barrel 107. The CCD frame 112 is aligned and fixed using multiple adjusting screws 114 and a fixing screw 115 which are formed on the lens barrel 107. A fixing V-shaped ditch 116 is formed on the outer circumference of the front end of the CCD frame 112. The fixing screw 115 is fitted into the V-shaped ditch 116. The CCD frame 112 is immobilized by a CCD frame presser 113.

The foregoing arrangement provides the position adjustment mechanism 106a or 106b. The position adjustment mechanism need be installed in only one of the optical systems.

When a relative position of a CCD with respect to an optical system is to be adjusted, first, the fixing screw 115 is loosened sufficiently. The multiple adjusting screws 114 are then loosened or tightened to move the CCD frame 112 relatively vertically or laterally as shown in FIG. 10. The CCD frame presser 113 is loosened to rotate the CCD frame 112, thus changing a relative angle of the CCD frame 112 with respect to the lens barrel 107. The position of the CCD frame 112 in the rotating direction is thereby adjusted. Thus, the CCD moves on a plane (image plane) perpendicular to the optical axis of an optical system. As a result, the position of the CCD with respect to the optical system can be adjusted.

After the adjustment of the relative position of the CCD has been completed, the fixing screw 115 is tightened. The CCD frame 112 is then brought back to the lens barrel 107 along the fixing V-shaped ditch 116 formed on the outer circumference of the front end of the CCD frame 112. The CCD frame presser 113 is then tightened to completely fix the CCD frame 112 to the lens barrel 107.

The positions of the centers of visual fields in images picked up by two CCDs can be made consistent with each other in a resultant observation image by adjusting the relative positions of CCDs with respect to optical systems. Consequently, a subject image with three-dimensionality can be observed.

Figure 11:
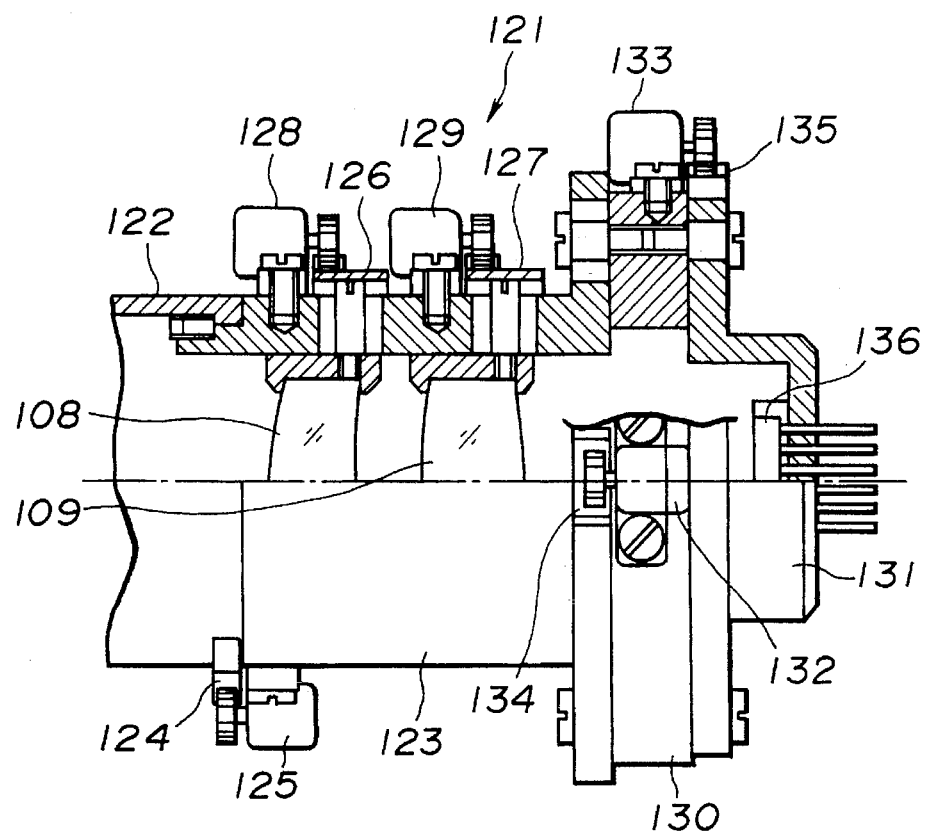
FIG. 11 is a partly cut-out cross-sectional view of a position adjusting mechanism for adjusting the relative position of a CCD by means of electrical drive.
Figure 12:
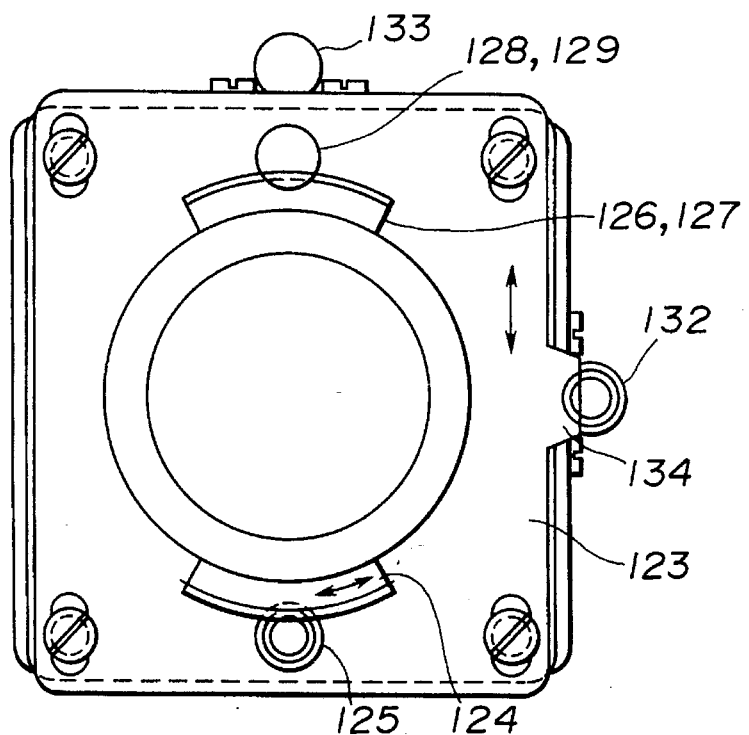
FIG. 12 is a plan view viewing the position adjusting mechanism in FIG. 12 from the front thereof.
Figure 13:
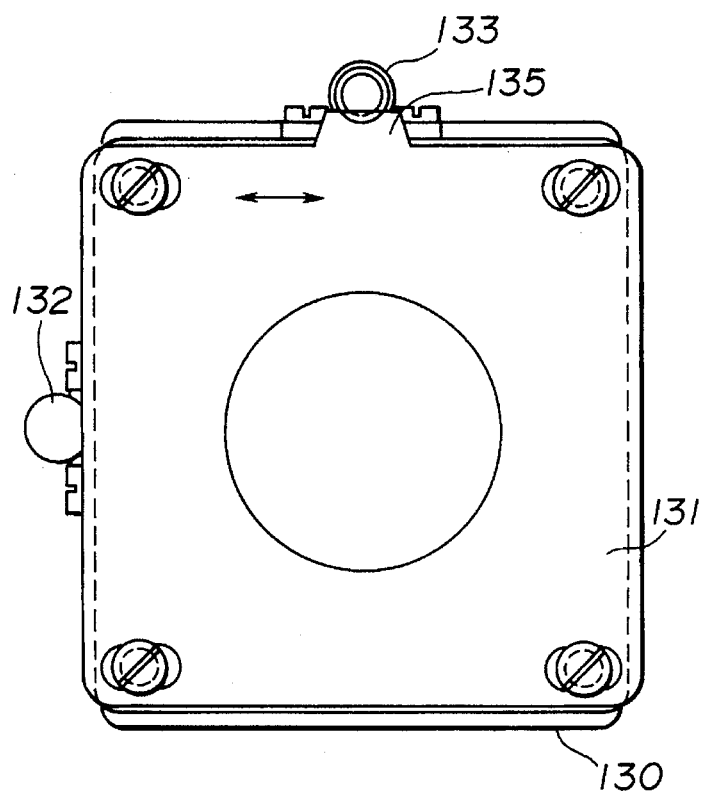
FIG. 13 is a plan view viewing the position adjusting mechanism in FIG. 12 from the back thereof.

FIGS. 11 to 13 show an example of an adjusting means that achieves adjustment by electrically driving an optical system. FIG. 11 shows a position adjustment mechanism 121 for adjusting the relative position of a CCD using electric drive. FIG. 12 views the position adjustment mechanism 121 from the front thereof (in the side of the optical system). FIG. 13 views the position adjustment mechanism 121 from the back thereof (in the side of the CCD).

A lens barrel 123 is attached to the back end of a stationary barrel 122 so as to be rotatable. A body of a motor 125 for rotating the lens barrel is fixed to the outer circumference of the lens barrel 123. A pinion formed on the rotation axis of the motor 125 is engaged with a gear 124 formed on the outer circumference of the stationary barrel 122. The lens barrel 123 includes a focusing lens system 108 and a variable magnification lens system 109 which are held by adjustment frames 126 and 127. The bodies of a focusing motor 128 and a magnification adjustment motor 129 are fixed to the outer circumference of the lens barrel 123. The pinions formed on the rotation axes of the motors are engaged with the gears on the adjustment frames 126 and 127. For focusing or other adjustment, the motors 128 and 129 are driven by means of drive circuits, which are not shown, to drive the adjustment frames 126 and 127. Thus, focusing or magnification adjustment can be achieved.

A displacement member 130 having a square cylindrical shape is mounted on the back end of the lens barrel 123 so as to be displaced vertically with respect to the lens barrel 123. A CCD frame 131 is mounted on the back end of the displacement member 130 so as to be displaced laterally with respect to the displacement member 130. A CCD 136 is locked in the CCD frame 131. The bodies of CCD position adjustment motors 132 and 133 are fixed to the outer circumference of the displacement member 130. A rack 134 is formed on the side surface of a rectangular collar at the end of the lens barrel 123. A pinion formed on the rotation axis of the motor 132 is engaged with the rack 134. A rack 135 is formed on the top of a rectangular collar at the front end of the CCD frame 131. A pinion formed on the rotation axis of the motor 133 is engaged with the rack 135. The displacement member 130 and CCD frame 131 are displaced by rotating the CCD position adjusting motors 132 and 133 by means of drive circuits which are not shown.

The foregoing arrangement provides the position adjustment mechanism 121.

When the relative position of a CCD with respect to an optical system is to be adjusted, the CCD position adjustment motor 132 is rotated by a drive circuit which is not shown. The displacement member 130 is then displaced vertically with respect to the lens barrel 123 as shown in FIG. 12. The motor 133 is rotated to displace the CCD frame 131 laterally with respect to the lens barrel 123 as shown in FIG. 13. The CCD is then aligned vertically and laterally. For adjustment in the rotating direction, a drive circuit, which is not shown, is used to rotate the lens barrel rotation motor 125. This causes the lens barrel 123, displacement member 130, and CCD frame 131 to rotate with respect to the stationary barrel 122. Thus, the CCD moves on a plane perpendicular to the optical axis of the optical system. Eventually, the position of the CCD is adjusted with respect to the optical system.

Similar to when the aforesaid mechanical adjustment means are employed, the positions of the centers of visual fields in images picked up by two CCDs can be made consistent with each other in a resultant observation image by adjusting the relative positions of CCDs with respect to optical systems. Consequently, a subject image with three-dimensionality can be observed.

Figure 14:
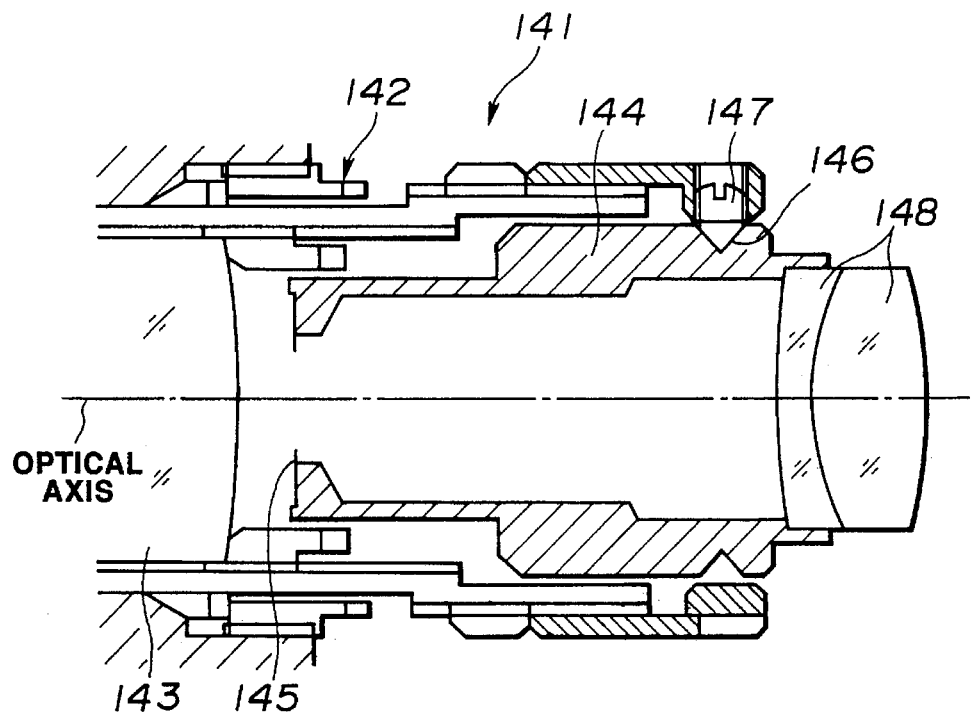
FIG. 14 is a cross-sectional view showing a structure of a visual-field mask moving mechanism.

As described above, when the relative positions of CCDs with respect to optical systems are adjusted, left and right visual field masks are mismatched due to a variation between the two optical systems. The visual field masks produce double images that are hard to see. A visual field mask moving mechanism 141 shown in FIG. 14 is installed to match the left and right visual field masks. Consequently, an excellent observation image suitable for three-dimensional vision is produced.

A relay lens system 143 is placed in a lens barrel 142. A mask tube 144 is placed behind the relay lens system 143 at the back end of the lens barrel 142. The front end of the mask tube 144 is provided with a visual field mask 145. A fixing V-shaped ditch 146 is formed along the outer circumference of the back end of the mask tube 144. Adjusting screws 147 formed on the lens barrel 142 are fitted into the V-shaped ditch 146. The adjusting screws 147 numbering, for example, three are formed along the circumference of the lens barrel 142. An eyepiece 148 is mounted at the back end of the mask tube 144. The foregoing arrangement provides a visual field mask moving mechanism 141. The visual field mask moving mechanism may be installed in only one of the optical systems or in both left and right optical systems.

Figure 15:
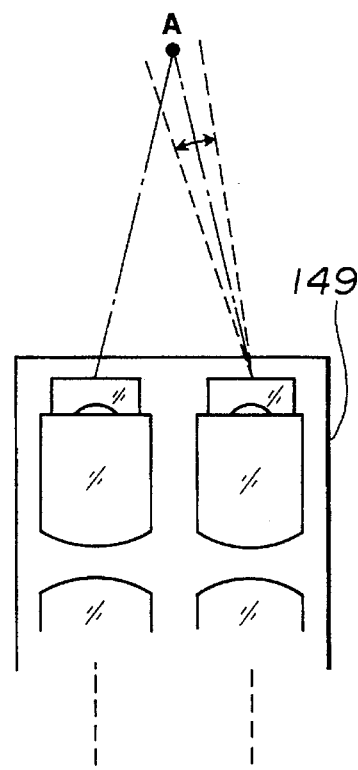
FIG. 15 is an explanatory diagram for explaining the operation of the visual-field mask moving mechanism.

For adjustment of a visual mask, the multiple adjusting screws 147 are loosened and tightened to move visual field masks 145, as shown in FIG. 15, vertically, laterally, and in the rotating direction with respect to optical systems. In a three-dimensional vision endoscope 149 in FIG. 15, one of the visual masks is a movable mask, and the other thereof is a stationary mask 150.

When the visual mask 145 is thus moved on a plane perpendicular to the optical axis of an optical system, the position of the visual field mask with respect to the optical system is regulated so that the center line of the stationary mask 150 will cross the center line of the movable mask 145. This allows left and right visual field masks to get consistent with each other. This results in an excellent observation image suitable for three-dimensional vision ensues.

Figure 16:
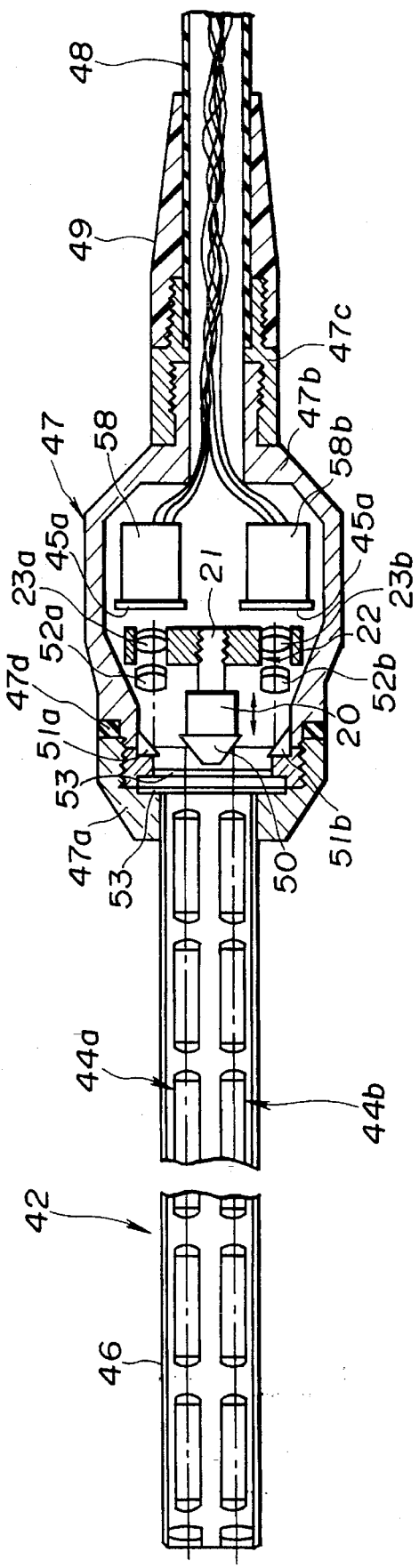
FIG. 16 shows a structure of a three-dimensional vision rigid endoscope having an automatic focusing mechanism.

A three-dimensional vision rigid endoscope 42 shown in FIG. 16 includes a focusing mechanism for automatic focusing. The endoscope 42 has the same components as those in the previous embodiment for the addition of the focusing mechanism. The same components will bear the same numerals, of which description will be omitted. Only different components and operation will be described.

A step motor 20 is located behind the prism 50 and locked in the holder body 47b. An axis 21 whose distal portion is male-threaded is projecting from the back of the step motor 20. A fixing member 22 whose center is female-threaded to engage with the male screw of the axis 21 at the distal portion thereof is locked in the holder body 47b. The fixing member 22 includes focusing lenses 23a and 23b that are placed between the fixed image formation lens 52a and CCD 45a, and between the fixed image formation lens 52b and CCD 45b.

In the foregoing arrangement, the step motor 20 is driven. The axis 21 then rotates slightly at a specified angle. The focusing lenses 23a and 23b move back and forth. The positions of the focusing lenses 23a and 23b each placed between the image formation lens and CCD can thus be controlled, and the focal distances on the CCDs 45a and 45b can be varied depending on the positions.

In the prior art, to achieve focusing, focusing must be performed on each of two imaging means. In a three-dimensional vision endoscope, it is necessary to display left and right images at substantially the same position and thus make left and right focal distances consistent with each other. Focusing is therefore complex.

In the three-dimensional vision rigid endoscope shown in FIG. 16, the focusing lenses in two optical systems are designed to be driven all together. Focusing is thus carried out. Left and right focusing can therefore be made consistent with each other easily. The step motor is controlled on the basis of the output signals of CCDs. Thus, an automatic focusing means is constituted.

Figure 17:
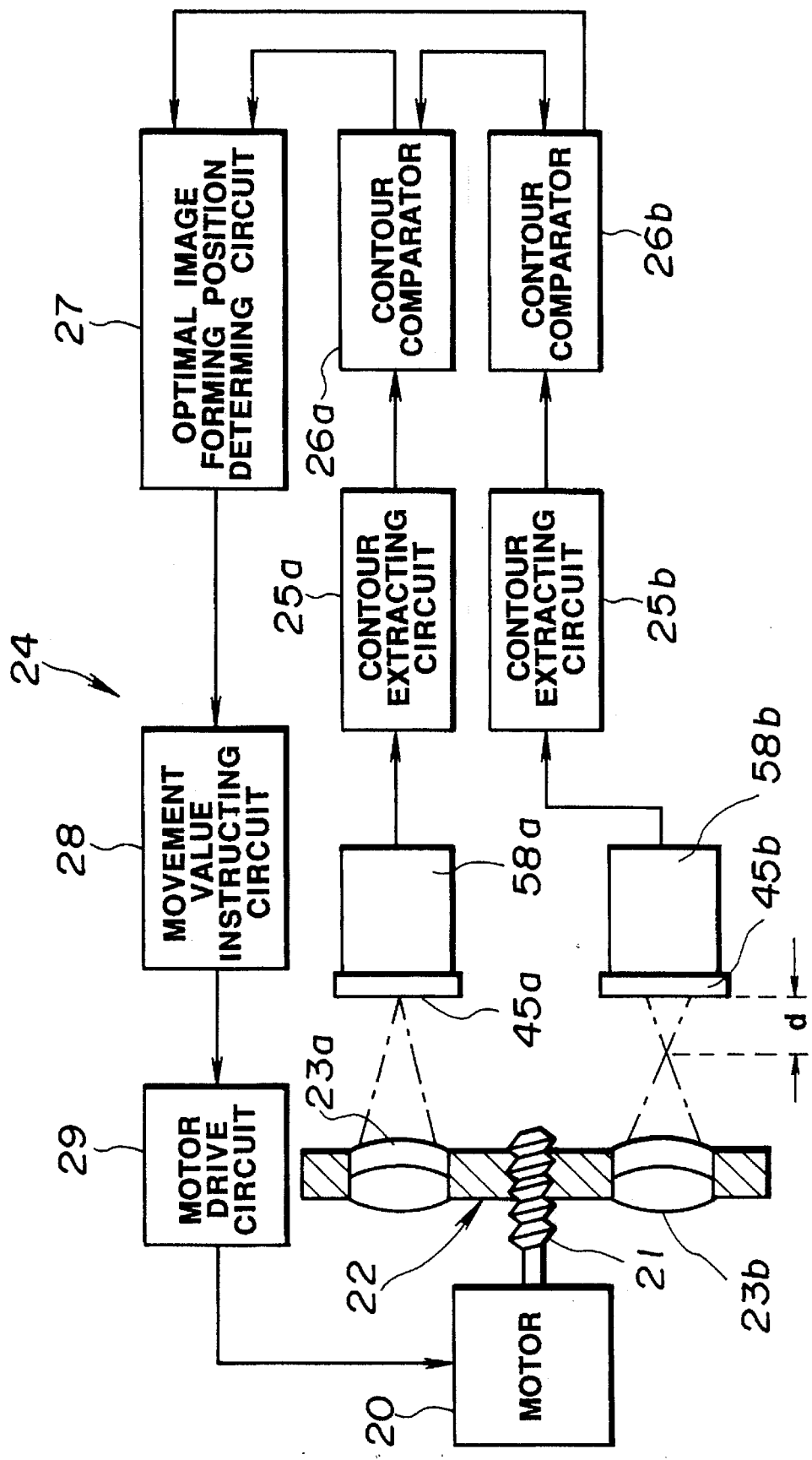
FIG. 17 is a block diagram showing a automatic focusing-related mechanism and electric circuitry.

FIG. 17 shows a automatic focusing-related mechanism and an electronic circuitry. Foci of left and right focusing lenses in an automatic focusing mechanism in FIG. 17 are shifted by a distance that does not cause an image on a screen to blur and that falls into a permissible range for both the left and right focusing lenses, which intends to minimize the time required for focusing. Reference numeral d in FIG. 17 denotes the permissible range of shifts for a set focus. An image on a screen will not blur at whatever points within the permissible range d of shifts the foci are set. In FIG. 17, the permissible range of shifts is exaggerated for better understanding.

An automatic focusing circuit 24 shown in FIG. 17 includes contour extracting circuits 25a and 25b for extracting contours of images from the outputs of the CCDs 45a and 45b, contour comparators 26a and 26b for comparing the extracted contours, and an optimal image forming position determining circuit 27 for detecting an optimal image forming position on the basis of the outputs of the contour comparators 26a and 26b.

The optimal image forming position determining circuit 27 provides a movement value instructing circuit 28 with an output. The movement value instructing circuit 28 drives the step motor 20 via a motor drive circuit 29.

In the foregoing arrangement, light beams emerging from the left and right focusing lenses 23a and 23b are focused on the left and right CCDs. When either of the light beams is in focus, the other beam is slightly out of focus. When the focusing lenses 23a and 23b are moved back and forth all together so as to come into focus, the time required for focusing can be minimized. This is because when the focusing lenses 23a and 23b come within the permissible range of shifts, d, the automatic focusing circuit 24 recognizes that the focusing lenses 23a or 23b are in focus. As described previously, this arrangement requires initial adjustment alone before left and right focusing get consistent with each other.

Figure 18:
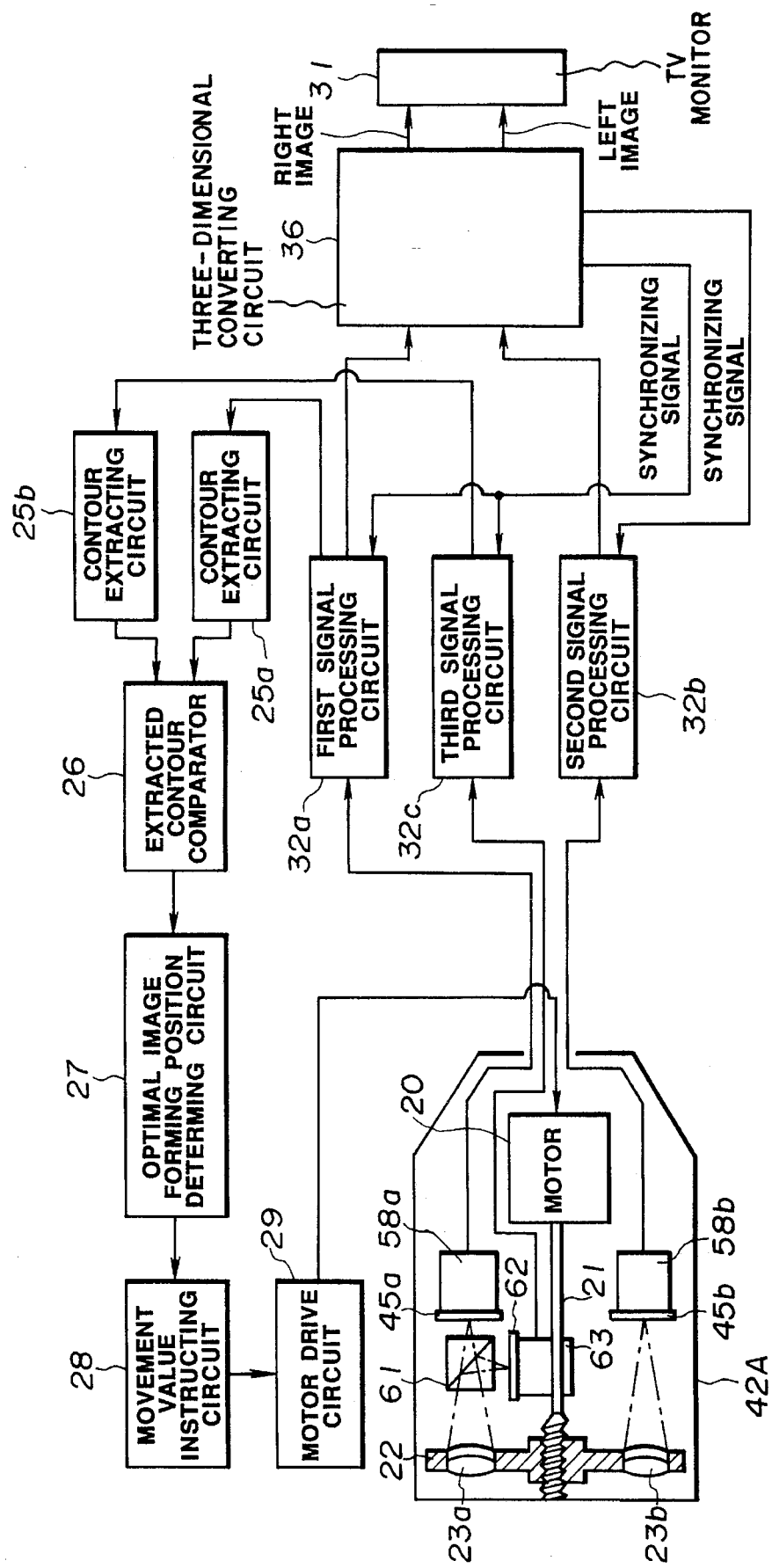
FIG. 18 schematically shows a configuration of a three-dimensional vision rigid endoscope apparatus relating to the variant in FIG. 17.

A three-dimensional vision rigid endoscope apparatus shown in FIG. 18 is a variant of the arrangement shown in FIG. 17.

In addition to the components shown in FIG. 16, a three-dimensional vision rigid endoscope 42A includes a half prism 61, an adjustment CCD 62, and peripheral circuits 63. The half prism 61 divides light transmitted by the focusing lens 23a into two beams. One of the two beams enters the CCD 45a, and the other thereof enters the adjustment CCD 62.

The CCDs 45a and 45b are separated by the same distance (focal distance) from the focusing lenses 23a and 23b. The relationships of the CCD 45a and adjustment CCD 62 are identical to those of the CCDs shown in FIG. 17; that is, the positions of the CCD 45a and adjustment CCD 62 are shifted within the permissible range d.

The automatic focusing circuit shown in FIG. 18 performs automatic focusing, similarly to the arrangement shown in FIG. 16, on the basis of the output signals of first and third signal processing circuits 32a and 32c. An extracted contour comparator 26 is formed by uniting the contour comparators 26a and 26b.

The monitor 31 displays left and right images sent from a three-dimensional signal processing circuit 36 for processing the outputs of first and second signal processing circuits 32a and 32b in order to construct a three-dimensional image. Three-dimensional observation is performed as described previously, of which description will therefore be omitted.

The arrangement shown in FIG. 18 has a drawback in that additional components are needed, which, however, provides an advantage over the arrangement shown in FIG. 17 in a point that imaging means for three-dimensional observation can be positioned at best focal points all the time. The other advantages are identical to those in the arrangement shown in FIG. 17.

Figure 19:
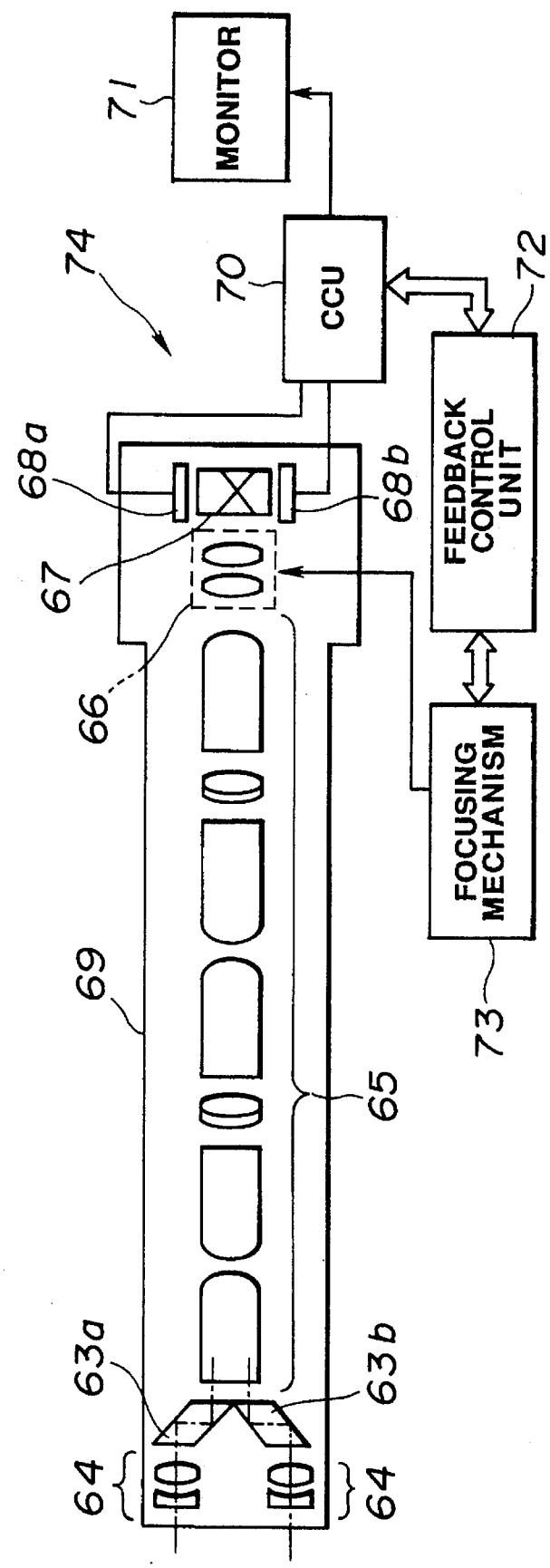
FIG. 19 is an explanatory diagram schematically showing an arrangement of a three-dimensional vision endoscope having a focusing mechanism and a mismatch value adjusting mechanism.

A three-dimensional vision rigid endoscope apparatus shown in FIG. 19 has an arrangement that adjustment is performed by relating a focused portion of an image (referred to as a focus area) with a portion thereof having naturalness and three-dimensionality (referred to as a three-dimensional vision area).

A three-dimensional vision rigid endoscope 69 in FIG. 19 includes two objective lenses 64, prism lenses 63a and 63b for changing the optical paths of incident light beams, a relay lens system 65 consisting of multiple lenses, and an image formation lens 66 located at the extreme end of the relay lens system 65. The relay lens system 65 transmits left and right subject images, which has a parallax between them, passing through the two objective lenses 64 concurrently but separately relative to pupils.

Left and right subject images formed by the image formation lens 66 are separated in directions perpendicular to the optical axis thereof by two built-in prisms 67, and then fed to CCDs 68a and 68b. The two prisms 67 are separated from each other.

Owing to the two CCDs, the three-dimensional vision rigid endoscope 69 provides left and right subject images having a parallax between them.

On the other hand, a CCD 70 shown in FIG. 19, similarly to the control unit 30 in FIG. 3, performs signal processing in order to display images on a monitor 71 for three-dimensional observation.

A feedback control unit 72 uses an internal signal of the CCU 70 to give an instruction to a focusing mechanism 73, so that the focus area and three-dimensional vision area will be matched at a certain ratio all the time.

The focusing mechanism 73 is a mechanism for moving the image formation lens 66 back and forth along the optical axis thereof, which includes, for example, a motor.

An example of the feedback control unit 72 is the automatic focusing circuit shown in FIGS. 17 and 18, or the optimal image forming position determining circuit 27 including a CPU which is not shown. The CPU sets data of appropriate values for the focus and three-dimensional vision areas. The CPU inputs a signal from, for example, the image mismatch detector 38, which is shown in FIG. 1, incorporated in the CCU 70, and then extends control as described below.

The CPU has data including a quantity of adjustment (appropriate value) for the focus area and a quantity of adjustment (appropriate value) for image mismatch. The CPU can adjust the focus and three-dimensional vision areas independently of each other so as to optimize the values of the respective areas.

In another control sequence, the CPU follows a built-in table that contains the quantities of adjustment for the focus area in association with the quantities of adjustment for image mismatch. When either of associated areas is adjusted, the other area is automatically adjusted according to the table. Thus, feedback control is achieved. When the focus area is to be adjusted, the CPU controls the focusing mechanism 73 according to the table. When image mismatch is to be adjusted, the CPU controls the memory control circuits 39a and 39b shown in FIG. 3, or the image mismatch detector 38 according to the table.

In a conventional three-dimensional vision rigid endoscope apparatus, the focus area and three-dimensional vision area are set irrelevant to each other and adjusted independently of each other. In an endoscope in which either the focus or three-dimensional vision area covers an entire image, only the other area should be adjusted. In an endoscope in which both the focus and three-dimensional vision areas are too small to overlap, both the areas should be adjusted. When the focus and three-dimensional vision areas are greatly deviated from each other, only limited portions of the areas are usable for observation.

In contrast with the prior art, in the three-dimensional vision rigid endoscope apparatus 74 shown in FIG. 19, whichever the focus or three-dimensional vision area is adjusted, the other area is adjusted automatically so that the focus and three-dimensional vision areas will be matched at a certain ratio all the time. An easy-to-see image ensues.

Figure 20:
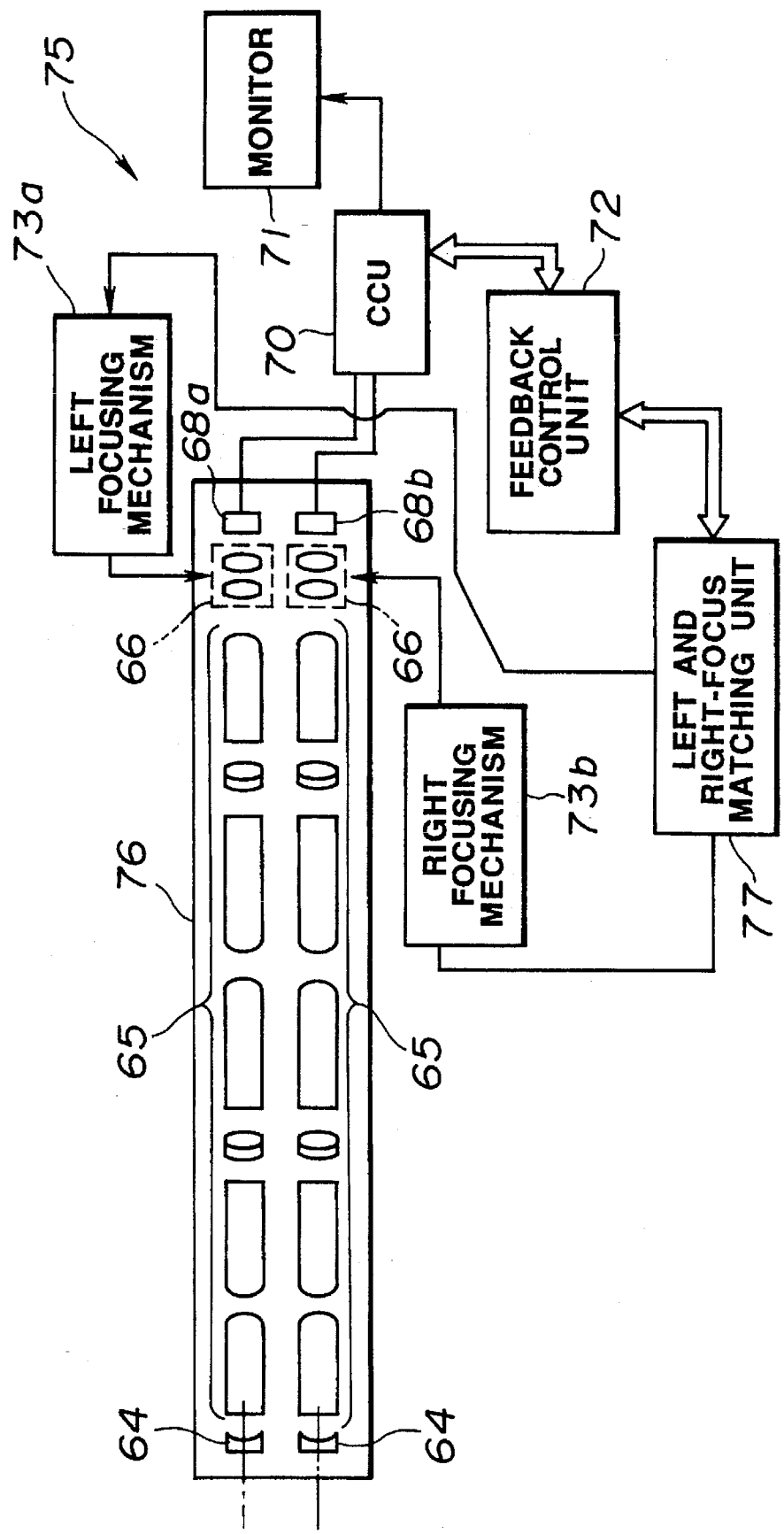
FIG. 20 is an explanatory diagram showing another arrangement of the three-dimensional vision rigid endoscope apparatus in FIG. 19.

A three-dimensional vision rigid endoscope apparatus 75 shown in FIG. 20 includes a three-dimensional vision rigid endoscope 76 instead of the three-dimensional vision rigid endoscope 69. The endoscope 76 does not have the prisms 63a, 63b, and 67, which are included in the components of the three-dimensional vision rigid endoscope 69, but includes two relay optical systems 65 and two image formation lenses 66. The other components and operation identical to those of the apparatus shown in FIG. 19 will bear the same reference numerals, of which description will be omitted.

The three-dimensional vision endoscope apparatus 75 has two objective lenses 66, which is therefore provided with two focusing mechanisms. The focusing mechanisms 73a and 73b receive an instruction from a feedback control unit 72 via a left and right focus matching unit 77. The left and right focus matching unit 77 performs matching so that the left and right objective lenses 66 will move in a well-balanced consistent manner. That is to say, the left and right focus matching unit 77 matches left and right foci.

When the structure shown in FIG. 16 is employed as a focusing mechanism, the left and right focus matching unit 77 becomes unnecessary. Nevertheless, the same advantages as those provided by the foregoing three-dimensional vision rigid endoscope apparatus 75 are available.

Figure 21:
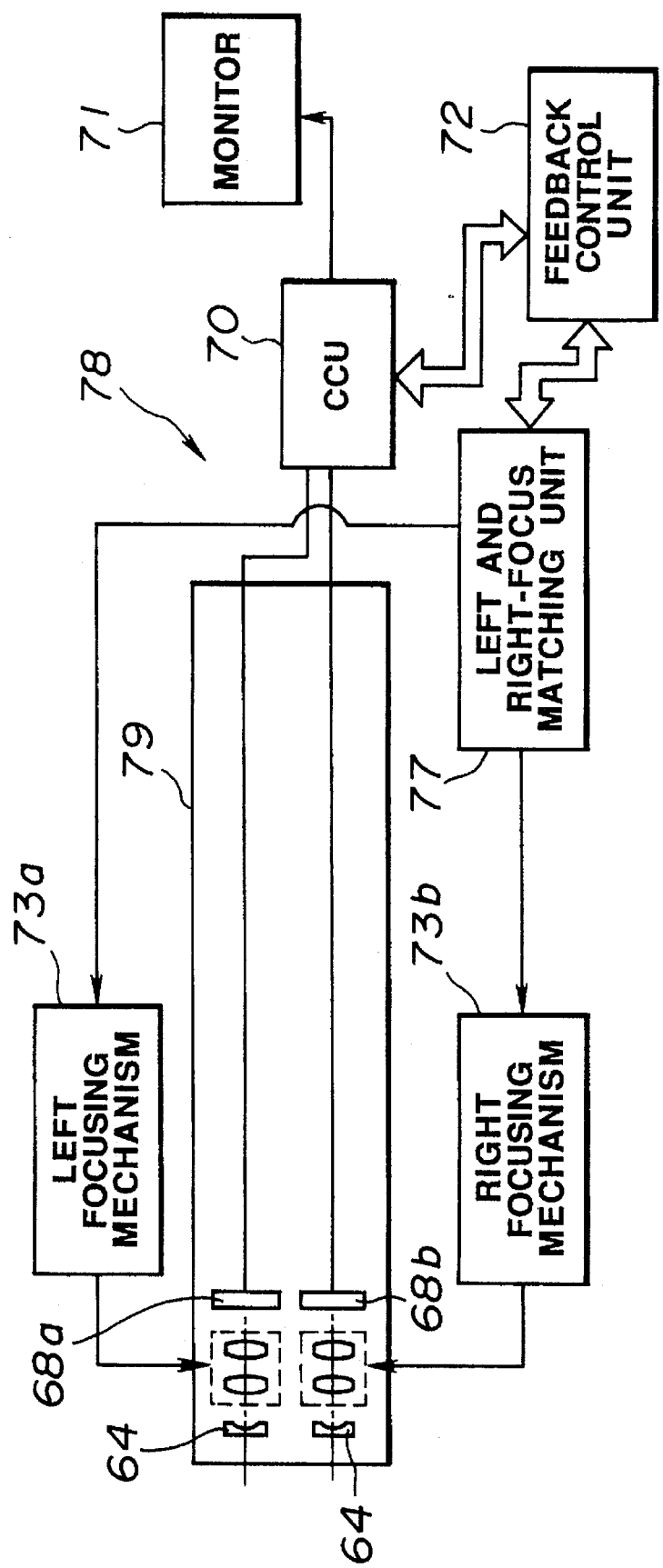
FIG. 21 is an explanatory diagram showing a yet another arrangement of the three-dimensional vision rigid endoscope in FIG. 19.

A three-dimensional vision rigid endoscope 78 shown in FIG. 21 does not have two relay optical systems 65, which are included in the three-dimensional vision rigid endoscope 76 shown in FIG. 20, but includes an endoscope 79 in which CCDs 68a and 68b are installed in the vicinity of the distal end thereof. The other components, and the operation and advantages are identical to those in the apparatus shown in FIG. 20. The components will bear the same reference numerals, of which description will be omitted.

Figure 22:
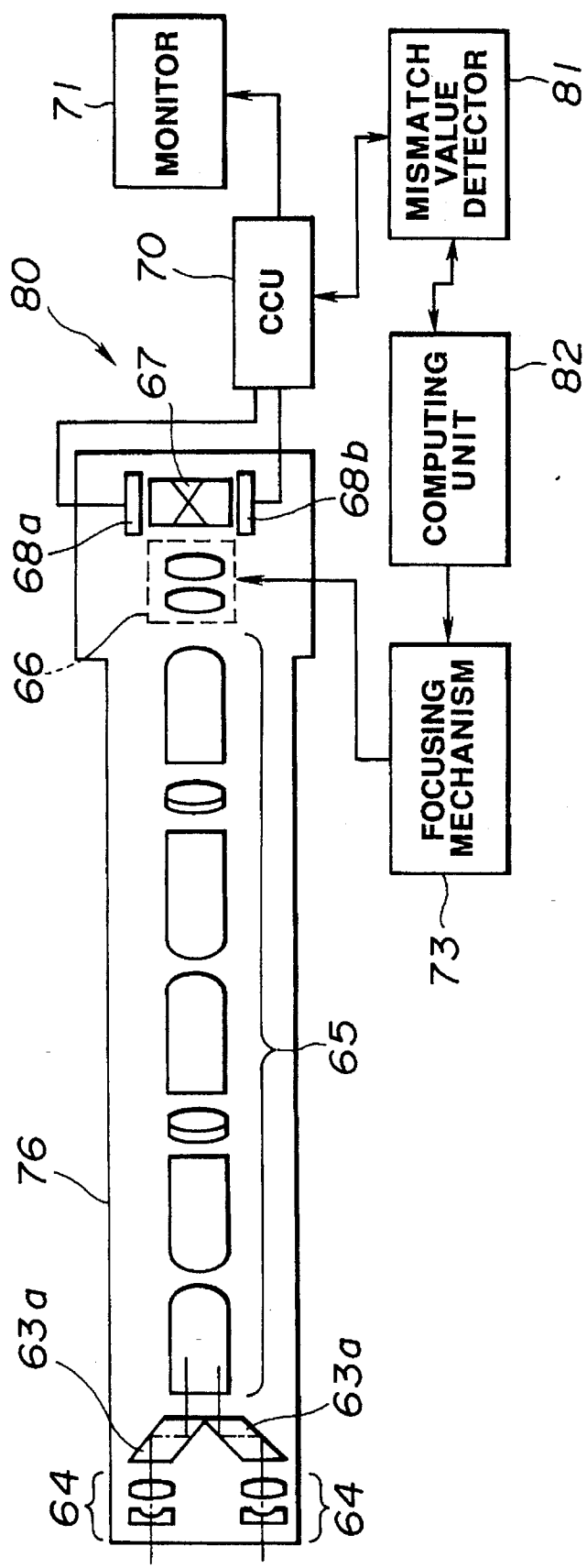
FIG. 22 shows an arrangement of a three-dimensional vision rigid endoscope in which a focusing range is restricted.

A three-dimensional vision rigid endoscope 80 shown in FIG. 22 includes a mismatch value detector 81 that detects a quantity of mismatch between left and right images over a region from a near point to a far point so that only the portions of left and right images, between which a quantity of mismatch is within a certain value, will come into focus, and a computing unit 82 for performing computation in comparing a detected quantity of mismatch with a three-dimensional vision area. The computing unit 82 performs focusing on an area (three-dimensional vision area) in which a quantity of mismatch is less than the certain value but does not perform focusing outside the three-dimensional vision area.

When a subject is located at a near point, the subject image comes into focus in a wide focal plane; that is, the left and right subject images are therefore mismatched. When a subject is located at a far point, the subject image is clearly divided into two portions. At either the near or far point, the resultant observation image is hard to see. The three-dimensional vision rigid endoscope 80 shown in FIG. 22 performs focusing only in the three-dimensional vision area permitting three-dimensionality (a permissible quantity of mismatch between left and right images). An area of an observation image originating from left and right images that are mismatched and seen separated from each other; such as, an observation image resulting from imaging of a subject at a near point or a far point is blurred. This prevents the entire observation image from becoming hard to see.

Figure 23:
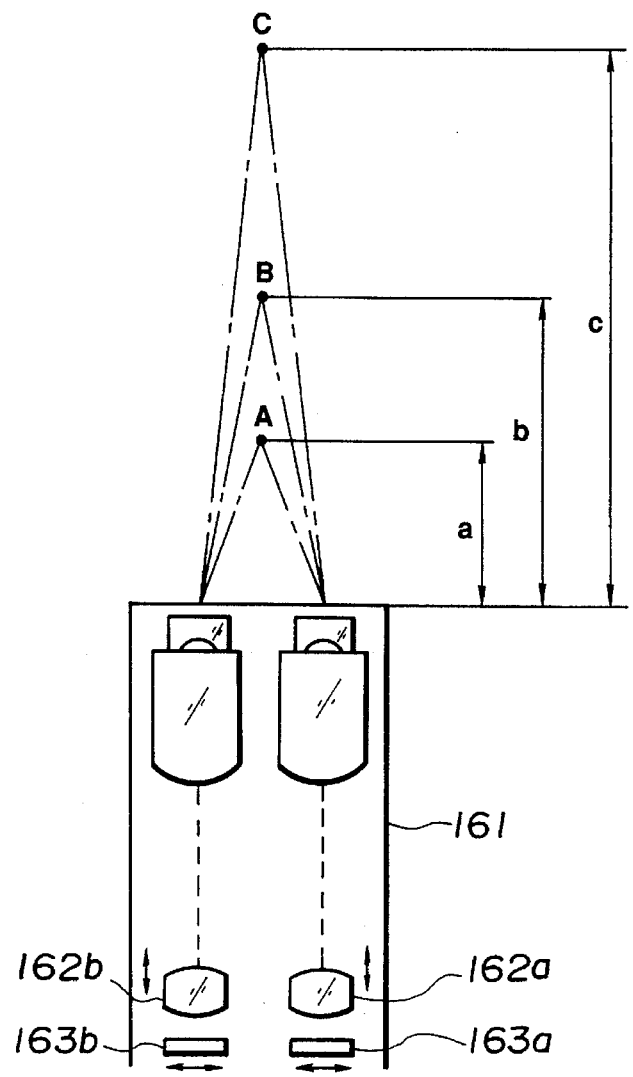
FIG. 23 is an explanatory diagram for explaining the relationships between a change in focal distance and a change in three-dimensional vision range.

The relationship between a shift in focal distance and a change in three-dimensional vision area will be described with reference to FIGS. 23 and 24.

In a three-dimensional vision endoscope 161, when a distance from a subject varies, focusing lenses 162a and 162b are moved back and forth along the optical axes thereof. A focal point is thus moved according to a subject. The optical axes of the left and right optical systems cross each other at a point different from the best focal point. This causes a point permitting three-dimensionality to differ from a focal point. The resultant observation image becomes very hard to see and causes an observer to feel fatigued soon. CCDs 163a and 163b are interlocked with the focusing lenses 162a and 162b, and moved on planes perpendicular to the optical axes thereof. The center points of subject images picked up by the CCDs are then displaced to match the best focal point and the intersection along visual fields between the left and right optical systems. For example, as shown in FIG. 23, a distance from the distal part of an endoscope to the best focal point is shifted to a, b, and c. Interlocked with the shift, the CCDs 163a and 163b moves so that the intersection along visual fields between the left and right optical systems will fall on A, B, and C.

Figure 24A:
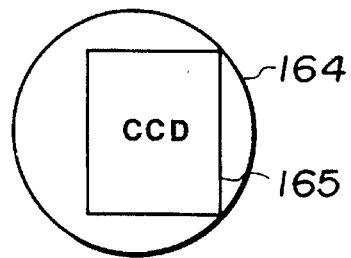
FIGS. 24a and 24b are explanatory diagrams each showing an image formation area for a subject image in a three-dimensional vision endoscope and an imaging area in a CCD.
Figure 24B:
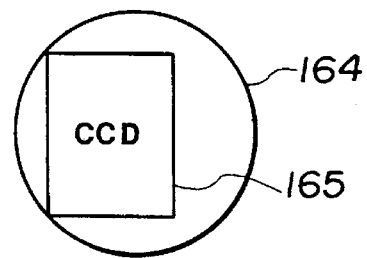

As shown in FIG. 24, a subject image is formed so that a formation area 164 of the subject image will be larger than an imaging region 165 of a CCD. Even when the CCD 163a or 163b is moved and the imaging region 165 of the CCD is displaced from a position shown in FIG. 21a to a position shown in FIG. 21b, the imaging region 165 of the CCD is still located within the formation region 164 of a subject image. The subject image can thus be displayed all over a monitor screen.

As described above, the best focal point and the intersection along visual fields between left and right optical systems are matched, thus allowing only the three-dimensional vision area permitting three-dimensionality to come into focus. This results in an excellent observation image suitable for three-dimensional vision, which does not fatigue an observer even when a distance to a subject varies.

In the present invention, it will be apparent that a wide range of embodiments can be formed on the basis of the invention without departing from the spirit and scope of the invention. This invention will be limited to the appended claims but not restricted to any specific embodiments.

What is claimed is:

1. A three-dimension vision endoscope apparatus comprising:

a pair of optical systems for transmitting an image of a subject as two subject images having a parallax between them;

a pair of imaging means for picking up said subject images transmitted by said optical systems;

a display means including a screen for displaying said two subject images either alternately or concurrently;

an adjusting means for adjusting said subject images to be displayed, said subject images being displayed at specified distances from positions at which subject images enter said optical systems, said subject images being positionally aligned on said screen of said display means by said adjusting means, wherein said adjusting means is a mechanical adjustment means for adjusting the position of at least one of said imaging means along a direction perpendicular to an optical axis of one of said pair of optical systems for transmitting said corresponding subject images; and a visual field mask position adjustment mechanism including adjusting screws and a mask tube, wherein said adjusting screws are used to change the relative position of said mask tube, said mask tube including a visual field mask lying in a lens barrel including one of said pair of optical systems.

2. A three-dimensional vision endoscope apparatus according to claim 1, wherein said visual field mask position adjustment mechanism is installed in both or either of proximal ends of said pair of optical systems.

* * * * *